(12) United States Patent
Zhao et al.

(10) Patent No.: US 9,539,290 B2
(45) Date of Patent: Jan. 10, 2017

(54) INDIVIDUALIZED BACTERIAL TREATMENT OF PANCREATIC CANCER

(71) Applicant: AntiCancer, Inc., San Diego, CA (US)

(72) Inventors: Ming Zhao, San Diego, CA (US); Fuminari Uehara, San Diego, AZ (US)

(73) Assignee: AntiCancer Inc., San Diego, CA (US)

( * ) Notice: Subject to any disclaimer, the term of this patent is extended or adjusted under 35 U.S.C. 154(b) by 87 days.

(21) Appl. No.: 14/140,345

(22) Filed: Dec. 24, 2013

(65) Prior Publication Data

US 2014/0178341 A1 Jun. 26, 2014

Related U.S. Application Data

(60) Provisional application No. 61/745,731, filed on Dec. 24, 2012.

(51) Int. Cl.
| | |
|---|---|
| *G01N 33/554* | (2006.01) |
| *G01N 33/569* | (2006.01) |
| *A61K 35/74* | (2015.01) |
| *C12N 1/20* | (2006.01) |
| *C12N 1/36* | (2006.01) |

(52) U.S. Cl.
CPC .............. *A61K 35/74* (2013.01); *C12N 1/20* (2013.01); *C12N 1/36* (2013.01)

(58) Field of Classification Search
None
See application file for complete search history.

(56) References Cited

PUBLICATIONS

Zhao et al. ( PNAS, vol. 102,No. 3, pp. 755-760, 2005).*
Hoffman ,R.M. (Amino Acid , vol. 37, pp. 509-521, 2009.*
Robert M. Hoffman, Bugging Tumors, cancerdiscovery. aacrjournals.org, Jul. 11, 2012, pp. 588-590, American Association for Cancer Research, United States of America.
John F. Toso, et al., Phase I Study of the Intravenous Administration of Attenuated *Salmonella typhimuium* to Patients With Metastic Melanoma, Jan. 2, 2002, pp. 142-152, vol. 20, No. 1, Journal of Clinical Oncology, United States of America.
Ming Zhao, et al., Monotherapy with a tumor-targeting mutant of *Salmonella typhimurium* cures orthotopic metastatic mouse models of human prostate cancer, Jun. 12, 2007, pp. 10170-10174, vol. 104, No. 24, PNAS, United States of America.
Chisa Nagakura, et al., Efficacy of a Genetically-modified *Salmonella typhimurium* in an Orthotopic Human Pancreatic Cancer in Nude Mice, 2009, pp. 1873-1878, AntiCancer Research 29, California, United States of America.
David M. Heimann, et al., Continuous Intravenous Administration of Live Genetically Modified *Salmonella Typhimurium* in Patients with Metastatic Melanoma, 2003, pp. 179-180, vol. 26, No. 2, Journal of Immunotherapy, Philadelphia, United States of America.
John Nemunaitis, et al., Pilot trial genetically modified, attenuated Salmonella expressing the *E. coli* cytosine deaminase gene in refractory cancer patients, 2003, pp. 737-744, vol. 10, Cancer Gene Therapy, Nature Publishing Group, Texas, United States of America.

* cited by examiner

*Primary Examiner* — J. Hines
*Assistant Examiner* — Khatol Shahnan Shah
(74) *Attorney, Agent, or Firm* — Schmeiser, Olsen & Watts LLP

(57) ABSTRACT

An individualized bacterial treatment of cancer is provided. The treatment includes a strain of bacteria modified by in-vivo passage through tumor grafts in experimental animals, where the modified strain exhibits enhanced cancer cell-targeting of a specific malignancy arising in a unique individual to the corresponding parent strain of bacteria. The treatment uses this modified strain for the treatment human solid-tumor malignancies by inoculating an individual with a quantity of the strain; and repeating inoculations at periodic intervals where repeated inoculations tend to progressively eliminate the solid tumor malignancy in the individual.

21 Claims, 2 Drawing Sheets

INDIVIDUALIZED BACTERIAL TREATMENT OF PANCREATIC CANCER

CROSS REFERENCE TO RELATED APPLICATION

This application claims priority from U.S. Patent Application No. 61/745,731, filed Dec. 24, 2012 and entitled "Individualized Bacterial Treatment of Pancreatic Cancer," which is incorporated entirely herein by reference.

BACKGROUND OF THE INVENTION

Technical Field

This invention relates to bacterial therapy for the treatment of cancer. In particular, the invention is highly customized "designer" strains of enhanced cancer cell-targeting bacteria for individualized cancer therapy, their method of creation, and their use in the treatment of human patients with cancer.

State of the Art

For at least three hundred years, those tending to the sick have occasionally observed regression of cancerous tumors in people suffering from severe acute infectious illnesses. At times, when the afflicted person survived an adequately severe and lengthy infection, the cancer completely disappeared resulting in a cure. In the late 19th and early 20th centuries, William B. Coley, a New York oncologist, infected cancer patients with *Streptococcus pyogenes* or administered extracts of the bacteria deemed "Coley's toxins, reportedly with remarkable results. (Hoffman, R. Bugging tumors. *Cancer Discovery* Jul. 11, 2012; p. 588.)

This phenomenon was largely ignored after Cooley's death in 1936, but interest in this unique form of cancer treatment has recently increased. The very conditions which make cancerous tumors resistant to conventional chemotherapy—an acidic pH microenvironment resulting from hypoxia and tumor necrosis—are favorable for the growth of anaerobic bacteria. Various genera of anaerobic bacteria, most notably *Clostridium* and *Bifidobacterium*, selectively infect necrotic regions of tumors over healthy tissue. But because these obligate anaerobes cannot establish infection in a non-hypoxic microenvironment, therapy with anaerobic bacteria must be combined with chemotherapy to kill viable solid tumors, small metastatic deposits, and individual cancer cells. Accordingly, *Salmonella*, a facultative anaerobe that exhibits sustained growth in both viable and necrotic regions of a tumor, has been shown to infect cancerous tumors, killing cancer cells in all regions of the tumor. Tumoricidal activity has also been noted in other genera of facultative anaerobes, such as *Streptococcus* and *Escherichia*.

To be an effective cancer treatment in vivo, a bacterial strain must not only be sufficiently cytotoxic to kill the cancer cells, but also unable to sustain an infection in normal tissues causing severe illness or death. Strategies employed to increase safety center around inducing mutations in wild-type bacteria, and then selecting for the mutated desired traits. Mutations decreasing the virulence of bacteria by altering the organism's ability to express cytotoxic characteristics, such as gene-based chemical changes of the wild-type lipopolysaccharide ("LPS") resulting in an attenuated host cytokine response are described. Also described are creating mutated strains auxotrophic for one or more nutrients, including purines and/or amino acids.

*S. typhimuruim* is a facultative anaerobe which can mount a sustained infection in both healthy and necrotic tissue. A strain of *S. typhimurium* auxotrophic for both arginine and leucine has been developed. Mutagenesis of a wild population of *Salmonella typhimuruim* is induced using nitrosoguanidine ("NTG"), and a resulting dual auxotroph for the amino acids leucine and arginine ("Leu-Arg") is selected from the heterogeneous population of auxotrophs, non-auxotroph mutations, and non-mutated wild bacteria. This Leu-Arg dual auxotroph (*S. typhimuruim* A1, or "A1") is unable to sustain an infection within somatic cells or normal tissue, but grows actively in individual cancer cells and malignant tumors. Otherwise, A1 has no other attenuating mutations limiting its cytotoxicity in infected tissues. *S. typhimurium*, therefore, has therapeutic potential. (Hoffman, R. Bugging tumors. *Cancer Discovery* Jul. 11, 2012; p. 588.)

Ideally, a bacterial strain 100% specific for the cancer of interest that is completely non-toxic to the host/patient is needed, along with a simple reproducible method for creating and using this strain in the treatment of human patients with cancer. No such strain exists in the prior art that even approaches this ideal, nor does a straightforward and reproducible method for producing such a strain.

Citation of documents herein is not an admission by the applicant that any is pertinent prior art. Stated dates or representation of the contents of any document is based on the information available to the applicant and does not constitute any admission of the correctness of the dates or contents of any document.

SUMMARY OF THE INVENTION

Embodiments of the present invention involve highly customized "designer" strains of enhanced cancer cell-targeting bacteria for individualized cancer therapy—sufficiently but not over-attenuated as not to cause sustained infection in normal tissues, their method of creation, and their use in the treatment of human patients with cancer.

An embodiment includes a strain of enhanced cancer cell-targeting bacteria for individualized cancer therapy comprising a modified strain of bacteria, wherein said modified strain is created by in-vivo passage through tumor grafts in experimental animals; and said modified strain exhibits enhanced cancer cell targeting of a specific malignancy arising in a unique individual compared to a corresponding unmodified strain of bacteria.

Another embodiment of the invention includes a method for creating a strain of enhanced cancer cell-targeting bacteria for individualized cancer therapy, said method comprises harvesting cancer cells from an individual; transplanting a quantity of said cancer cells into a quantity of experimental animals; incubating the experimental animals to establish a cancer tissue graft within the experimental animals; inoculating a quantity of bacteria$_{A1}$ into a said experimental animal containing established said cancer tissue graft; removing said cancer tissue graft from the said experimental animal following a period of in-vivo incubation; extracting bacteria$_R$ from said cancer tissue graft removed from the experimental animal; incubating said bacteria$_R$ under conditions suitable for bacterial multiplication; selecting said bacteria$_R$; incubating said bacteria$_R$ under conditions suitable for bacterial multiplication; inoculating a quantity of bacteria$_R$ into a second said experimental animal containing established said cancer tissue graft; removing said cancer tissue graft from the second said experimental animal following a period of in-vivo incubation; extracting bacteria$_{R1}$ from said cancer tissue graft removed from the second said experimental animal; incubating said bacteria$_{R1}$ under conditions suitable for bacterial multiplication; selecting said bacteria$_{R1}$; and incubating said bacteria$_{R1}$ under conditions suitable for bacterial multiplication.

Yet another embodiment includes a method for treatment of human solid-tumor malignancies using a strain of enhanced cancer cell-targeting bacteria for individualized cancer therapy. The method comprises harvesting cancer cells from an individual with a solid-tumor malignancy; creating tumor xenografts in immunologically deficient experimental animals with harvested said cancer cells; selecting a strain of enhanced cancer cell-targeting bacteria by serial in-vivo passage of said bacteria through said tumor xenografts within said experimental animals; performing extraction, isolation, and propagation of said strain; performing inoculation of said individual with a quantity of said strain; and repeating inoculations at periodic intervals of a quantity of said strain in said individual wherein repeated inoculations tend to progressively eliminate said solid tumor malignancy in said individual.

The foregoing and other features and advantages of the present invention will be apparent from the following more detailed description of the particular embodiments of the invention, as illustrated in the accompanying drawings.

DETAILED DESCRIPTION OF EMBODIMENTS OF THE INVENTION

Figure 1:
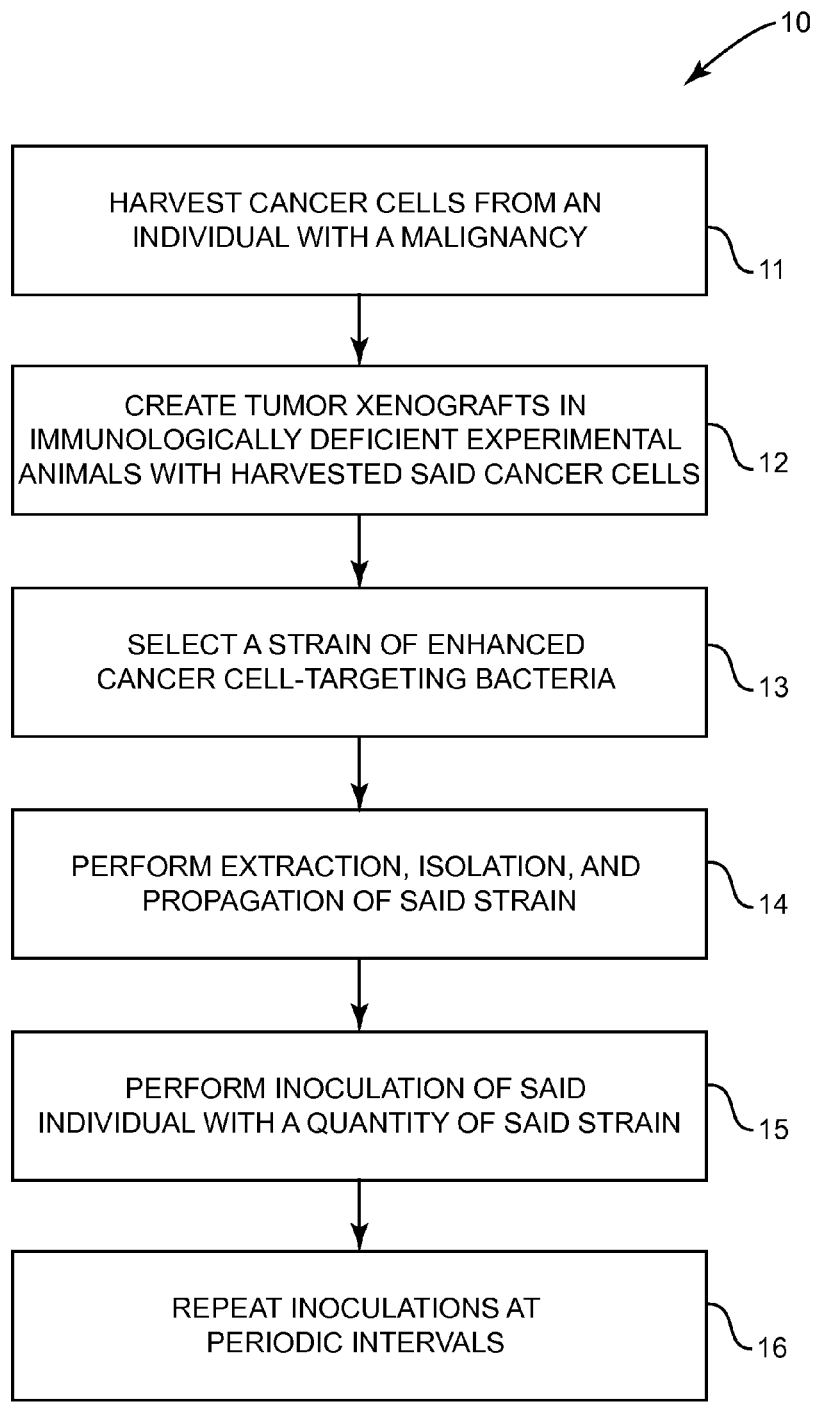
FIG. 1 is a flow chart of a method of individualized bacteria treatment of cancer.

Since the discovery of vaccines and antibiotics to prevent and treat infectious disease, cancer has become a leading cause of death in adults over the age of forty-five. Only heart disease is responsible for more deaths annually. Despite the magnitude of this disease, finding curative treatments for cancer has been difficult. Cancer can arise from virtually any cell type. Cancers are genetically unstable and often develop a phenotypically heterogeneous cell population early in their course. This heterogeneity leads to variable responses to treatment within the same patient, including resistance. Through the process of multiplication, local invasion, and metastasis, cancer cells become interspersed within normal tissue, like weeds in a lawn. To permanently rid the lawn of weeds, every individual weed must be killed, lest even one resistant weed survive to multiply and re-infest the entire lawn. Eliminating the weeds, however, cannot be at the expense of destroying the lawn.

Current treatment strategies include surgical resection, chemotherapy, radiotherapy, and various combinations of these modalities. The choice of treatment depends on the cell type of the tumor and the stage of the cancer at the time treatment is initiated. All of these treatments have some degree of limited efficacy and patient toxicity. Surgery is impractical when multiple or widespread metastases are present. Where the disease is locally advanced and invades surrounding structure vital for survival, surgery is of limited or no value. Surgery for cancer is also highly invasive and comes with all of the risks and side effects associated with surgery for benign conditions. The well-known side effects of chemotherapy are, at best, miserable; and at worst, fatal. Chemotherapy kills asymptotically. With the exception of small-cell lung cancer and certain lymphoid, hematogenous, and germ-cell malignancies, chemotherapy always leaves a percentage of viable cancer cells. Therefore, chemotherapy is typically not curative. And because chemotherapy is unable to kill every cell, chemotherapy selects for those cell types most resistant to treatment. Like chemotherapy, radiotherapy also kills asymptotically and selects for resistant cell lines. Depending on the size of the radiated field, the type of surrounding tissue, and the total dose of radiation, the side effects of radiotherapy may be limited or severe.

Like conventional chemotherapy and radiotherapy, the use of bacterial infectious agents to treat cancer would be similarly limited by the current state of the art. Bacterial treatment of cancer must temper cytotoxicity with specificity, restricting an otherwise harmful infection to cancer cells and tumors.

Current strategies to maximize patient safety focus on reducing the virulence of the bacterial strain used for treatment. These include exposing a wild population of bacteria to mutagenic agents, then selecting strains with attenuated pathogenicity. Examples are strains that produce a fractional amount of a cytokine or direct cytotoxin as those produced by the corresponding wild strains. Reducing virulence, however, may lead to reduced tumor targeting and decreased cytotoxicity. An attenuated strain of *S. typhimurium* showed limited, if any, effectiveness in treating metastatic malignant melanoma patients in a phase I clinical trial, possibly because it was over-attenuated. (Toso, J. F. et al. Phase I study of the intravenous administration of attenuated *Salmonella typhimurium* to patients with metastatic melanoma. *J. Clin Oncol.* 20: 142-52 (2002).) In this study, the bacterial agent utilized was a *S. typhimuruim* with two induced mutations; purI (creating an auxotroph for the purine adenine), and msbB. The msbB mutation altered the bacterial lipopolysaccharide ("LPS") such that upon infection in mice, the normal host cytokine response was markedly attenuated. Ten-fold lower levels of TNFα were measured in mice infected with this mutant strain, versus mice infected with the corresponding non-mutated *S. typhimurium*, which all died.

To be therapeutically efficacious, the "safe" bacterial strain must also be able to infect cancer cells and tumors with the highest degree of selectivity. Although the *S. typhimurium* containing the purI and msbB mutations was demonstrated to concentrate in tumors versus non-cancerous tissue at ratios greater than 250:1, described as "tumor targeting," this "targeting" is merely preferential replication of bacteria in a more favorable tumor microenvironment. This is an endogenous characteristic of wild strains of bacterial species, demonstrated by the historical anecdotes of occasional cures of cancer patients surviving life-threatening infections. Further, the *S. typhimurium* purI/msbB strain (*S. typhimurium* VNP20009) only demonstrated minimal "tumor targeting," selectively colonizing tumors in only some patients in three published human clinical trials, deemed unsuccessful in treating solid tumor cancers in human patients. (3 out of 25 patients: Toso, J. et al. Phase I study of the intravenous administration of attenuated *Salmonella typhimurium* to patients with metastatic melanoma. *J. Clin. Oncol.* 20, 142-52 (2002); 1 out of 4 patients: Heimann, D. M. et al. Continuous intravenous administration of live genetically modified *Salmonella typhimurium* in patients with metastatic melanoma. *J. Immunother.* 26, 179-80 (2003); 2 out of 3 patients: Nemunatis, J. et al. Pilot trial of genetically modified attenuated *Salmonella* expressing the *E. coli* cytosine deaminase gene in refractory cancer patients. *Cancer Gene Ther.* 10, 737-44 (2003).) Therefore, the prior art demonstrates that *S. typhimuruim* VNP2009 is lacking in both virulence and tumor-targeting for the treatment of human solid tumor cancers. A different genetically-engineered, strain of bacteria is needed to overcome these characteristic lacking in *S. typhimurium* VNP2009, other strains of *Salmonella*, and other bacterial genera.

Additional examples of reducing virulence by selection of mutated bacterial strains auxotrophic for one or more nutrients, including purines and amino acids, are noted in the prior art. A mutant strain of *S. typhimurium* auxotrophic for leucine and arginine, "*S. typhimurium* A1", has no impairment of LPS, other cytokine-inducing substances, or cytotoxins where the required nutrients are present. This dual auxotroph, however, is unable to sustain an infection in normal somatic tissues, making it potentially safe for use as a therapeutic agent.

Thus, the A1 dual auxotroph variant is able to kill cancer cells but not infect normal tissues. The strain can then be further enhanced by selecting for tumor-targeting sub-strains in a nude mouse model. Nude mice harboring human colon cancer orthotopic tumorgrafts (xenografts) are infected with A1 and the bacteria are subsequently extracted directly from the tumorgrafts following a period of incubation. This "reselected" strain is denoted "A1-R." A1-R was able to eradicate primary and metastatic tumors in mono-therapy in the orthotopic-transplant nude mouse models of human prostate (Zhao, et al. Mono-therapy with a tumor-targeting mutant of *Salmonella typhimuruim* cures orthotopic metastatic mouse models of human prostate cancer. *Proc. Natl. Acad. Sci. USA* 104: 10170-74 (2007)); breast (Zhao, M. et al. Targeted therapy with a *Salmonella typhimuruim* leucine-arginine auxotroph cures orthotopic human breast tumors in nude mice. *Cancer Res.* 66: 7647-52 (2006)); and pancreatic cancer (Nagakura, C. et al. Efficacy of a genetically-modified *Salmonella typhimurium* in an orthotopic human pancreatic cancer in nude mice. *Anticancer Res.* 29: 1873-78 (2009)). In the above studies, nude mice engrafted with human tumors tolerated tail vein injection of $10^7$ colony forming units ("CFUs") of the *S. typhimurium* A1-R dual auxotroph with apparent systemic effects. All showed substantial tumor regression and a high percentage were completely cured, depending on the primary cancer cell type.

What is lacking in the prior art, however, is a strain of bacteria that is custom-produced with the highest specificity to target not merely an individual cancer cell type, but a genetically and phenotypically unique malignancy arising within an individual patient—a "designer bug" for each patient that, at a minimum, preserves all of the cytotoxicity of the native strain of bacteria while being unable to sustain an infection in non-cancerous somatic cells and healthy tissues.

This invention addresses both of these fundamental requirements—safety and specificity—by creating a unique, modified strain of reselected auxotrophic bacteria using a novel method. The result is a bacterial agent with a maximally-enhanced, highest possible specific targeting of cancer cells wherever they exist in the body while limiting host toxicity and not causing significant illness, custom-tailored to the unique malignancy present in a single individual patient. This invention discloses such a strain, and further discloses a simple, reproducible method for creating additional modified strains for enhanced cancer-cell targeting of a specific malignancy arising in a unique individual. Additionally, the invention discloses a method of using the strain for the treatment of human patients with cancer.

Disclosed are strains of enhanced cancer cell-targeting bacteria for individualized cancer therapy comprising a strain of bacteria modified by in-vivo passage through tumor grafts in experimental animals, wherein said modified strain exhibits enhanced cancer cell-targeting of a specific malignancy arising in a unique individual compared to the corresponding parent strain of bacteria.

FIG. 1 shows a method 10 for treatment of human solid-tumor malignancies using a strain of enhanced cancer cell-targeting bacteria for individualized cancer therapy. The method 10 comprises Step 11 of harvesting cancer cells from an individual with a malignancy. Once the cancer cells are harvested, the method 10 includes Step 12 of creating tumor xenografts in immunologically deficient experimental animals with said harvested cancer cells. The method 10 then includes a Step 13 of selecting a strain of enhanced cancer cell-targeting bacteria by serial in-vivo passage of said bacteria through said tumor xenografts within said experimental animals. Following Step 13, Step 14 is executed of performing extraction, isolation, and propagation of said strain. The method then includes Step 15 of performing inoculation of said individual with a quantity of said strain. The method 10 then may include repeating inoculations at periodic intervals of a quantity of said strain in said individual wherein repeated inoculations progressively eliminate said malignancy in said individual.

Figure 2:
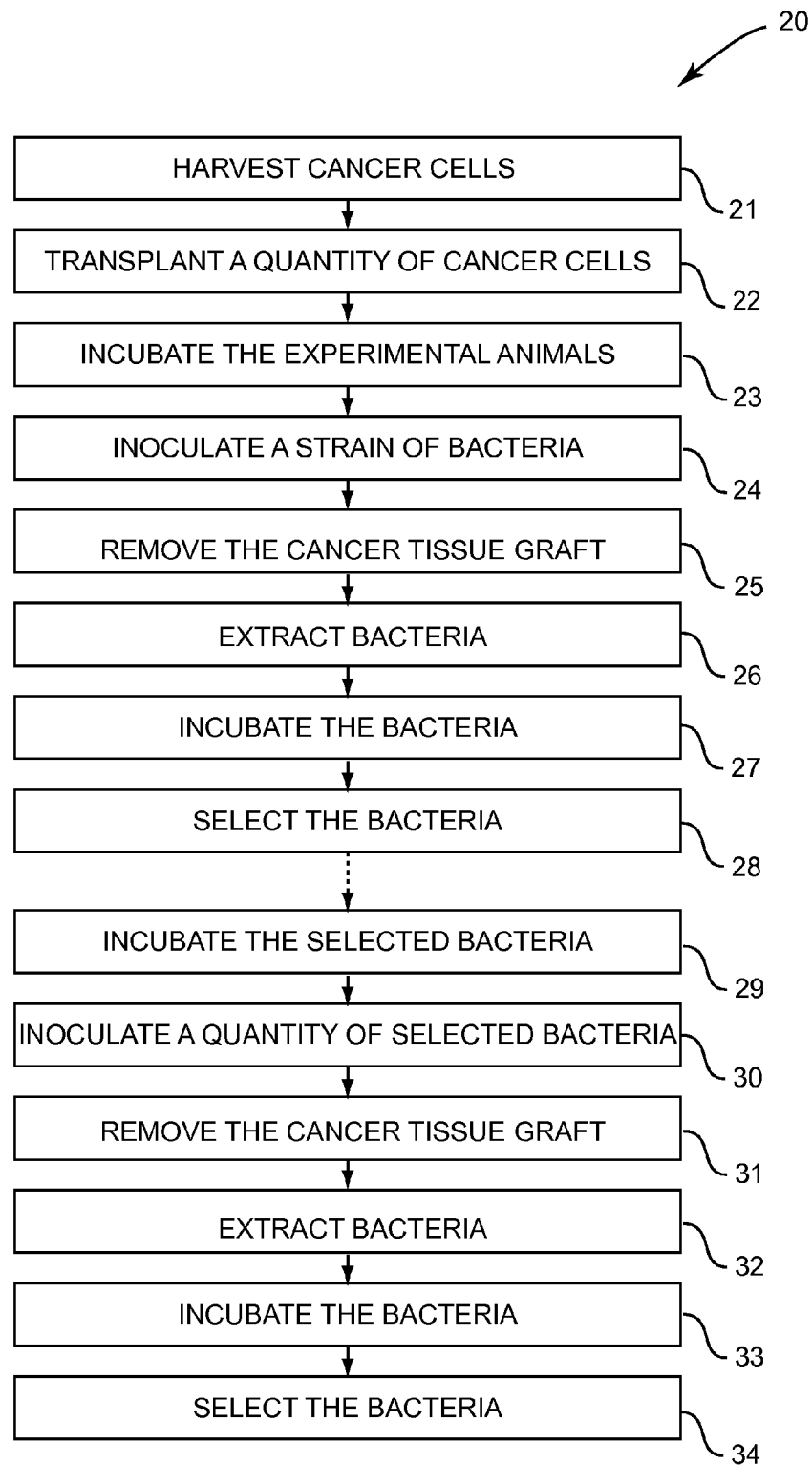
FIG. 2 is a flow chart of another method of individualized bacteria treatment of cancer.

FIG. 2 depicts another method 20 for treatment of human solid-tumor malignancies using a strain of enhanced cancer cell-targeting bacteria for individualized cancer therapy. The method 20 comprises Step 21 of harvesting cancer cells from an individual. Step 21 is followed by Step 22 of transplanting a quantity of said cancer cells into a quantity of experimental animals. After transplanting a quantity of cancer cells into the experimental animals, Step 23 includes incubating the experimental animals to establish a cancer tissue graft within the experimental animals. Step 23 leads to Step 24 of inoculating a bacterial strain$_{A1}$ into a said experimental animal containing established said cancer tissue graft. The method 20 further includes Step 25 of selecting a number of killed cancer cells infected with the bacteria$_{A1}$. The method 20 may then include removing said cancer tissue graft from said experimental animal inoculated with said bacterial strain following a period of in-vivo incubation. The method 20 further comprises Step 26 of extracting bacteria$_R$ from said cancer tissue graft removed from the experimental animal inoculated with said bacterial strain; Step 27 of incubating said bacteria$_R$ under conditions suitable for bacterial multiplication; Step 27 of inoculating a quantity of said bacteria$_R$ into a second said experimental animal containing established said cancer tissue graft; and Step 28 of selecting a said bacteria.

Additional embodiments of the invention may continue with steps 29-35 of Method 20. Step 29 of incubating the selected said bacteria$_R$ under conditions suitable for bacterial multiplication is followed by Step 30 inoculating a quantity of selected said bacteria$_R$ into a second said experimental animal containing established said cancer tissue graft; Step 31 removing said cancer tissue graft from the said experimental animal inovulated with a quantity of said bacteria$_R$ following a period of incubation; Step 32 extracting bacteria$_{R1}$ from said cancer tissue graft removed from the experimental animal; Step 33 incubating said bacteria$_{R1}$ under conditions suitable for bacterial multiplication; and Step 34 selecting a said bacteria$_{R1}$.

Referring to FIGS. 1 and 2, the methods 10 and 20 may further include creating a strain of enhanced cancer cell-targeting bacteria for individualized cancer therapy, said method comprising the steps of harvesting cancer cells from an individual (experimental animal or human); transplanting a quantity of said cancer cells into a quantity of experimental animals; incubating the experimental animals to establish a cancer tissue graft within the experimental animals; inoculating a bacterial strain$_{A1}$ into a said experimental animal containing established said cancer tissue graft; removing said cancer tissue graft from said experimental animal inoculated with said bacterial strain$_{A1}$ following a period of incubation of the inoculated said experimental animal; extracting bacteria$_R$ from said cancer tissue graft removed from the experimental animal inoculated with said bacterial strain$_{A1}$; incubating said bacteria$_R$ under conditions suitable for bacterial multiplication; inoculating a quantity of said bacteria$_R$ into a second said experimental animal containing established said cancer tissue graft; removing said cancer tissue graft from the second said experimental animal following a period of in-vivo incubation; extracting bacteria$_{R1}$ from said cancer tissue graft removed from the experimental animal; and incubating said bacteria$_{R1}$ under conditions suitable for bacterial multiplication.

In one embodiment of the methods 10 and 20, the bacteria are a modified strain of *Salmonella typhimuruim* ("*S. typhimurium*"). This is not meant to be limiting, and strains of other facultative anaerobes, for example *Salmonella, Streptococcus, Escherichia*, and others may be used in various embodiments of the invention. Mutations are induced in the wild strain and mutants are selected for ability to grow in cancer cells and/or tumors without sustaining an infection in non-cancerous host tissues and cells using any variety of established techniques known to those skilled in bacterial genetic engineering and related arts.

Further, intracellular replication and virulence of *S. typhimurium* A1 or A1-R can be directly observed by transfecting *S. typhimuruim* A1 with the green fluorescent protein ("GFP") gene pGFP using electroporation. In other embodiments, the nuclei and cytoplasm of the engrafted cancer cells can also be labeled through stable transposition of retroviral red fluorescent protein ("RFP") in the cytoplasm and retroviral GFP in the nucleus (by fusion of GFP with histone H2B). Other labeling techniques may also be used. This combination enhances the initial selection of bacteria that are tumor targeting by allowing for the visualization of the bacterial cancer cell interaction using dual color spatial-temporal fluorescence microscopy. Apoptosis of the infected cancer cells is readily determined by observing fragmentation of the GFP-expressing nuclei. Cells with intact nuclei after a period of incubation not containing cytotoxic bacteria are distinguished from apoptotic cells specifically targeted and killed by intracellular cytotoxic bacteria. In embodiments of the invention, only those killed cancer cells harboring cytotoxic bacteria are selected for isolation and propagation of the intracellular bacteria. This resulting "reselected" strain is denoted A1-R$_n$ were "n" is zero or a whole number representing the number of selection cycles, either in-vitro or in-vivo, undergone by the original A1 strain.

According to the methods 10 and 20, to create orthotopic tumorgrafts (xenografts) in the nude mouse model, human cancer cells or biopsy samples of tumor tissue taken directly from the cancer patient are used. The immunologically deficient athymic "nude" mouse is used by way of example because this is the most commonly used model today. The invention is intended to cover the creation of human patient tumor xenografts using the family of procedures established in the prior art with immunologically deficient mice and other suitable experimental animals.

In various embodiments of the invention, and according to methods 10 and 20, harvested cancer tissue may be homogenized with the individual cells isolated, grown in tissue culture and inoculated via the tail vein. The harvested cancer tissue may be individual cancer cells harvested from a variety of sources, including but not limited to patient blood (circulating tumor cells), sputum (lung cancer), vaginal or endocervical swabs, malignant ascites, and malignant pleural effusions. Alternatively, the grafts may be surgically transferred directly to a favorable host organ or tissue within the immunologically deficient mouse. In various embodiments of the invention, this may be accomplished by surgically implanting a 1 mm to 3 mm block of tissue beneath the capsule of the host organ in the anesthetized animal, such as the pancreas or prostate, into the mammary fat pad, or sub-serosally into the cecal wall, depending on the cell type of the primary tumor. This establishes a xenograft, whereby the human cancer grows and metastasizes within the mouse or other experimental animal, continuing to demonstrate the same phenotype—including human histopathology and tumor-marker production—as the original human tumor.

Embodiments of the invention may be practiced with an in in-vitro inoculation of the parent strain of bacteria A1 into harvested cancer cells grown in tissue culture, incubation, selection of bacterial strain$_{Rn}$ from infected, killed cancer cells in vitro, followed by any number of iterations passaging the selected bacterial strain$_{Rn}$ through tumor xenografts in vitro. In other embodiments if the invention, the in-vitro passage of the selected bacterial strian$_{Rn}$ may be performed at any point following step 23 or step 29 of the method 20. Embodiments of the invention may be practiced using one, or greater than one in-vitro passage of the selected bacterial strain$_{Rn}$. Other embodiments may omit this in-vitro passage cycle. Still other embodiments may use in-vitro passage cycles only, with no passage through in-vivo tumor xenografts. The foregoing embodiments utilizing at least one passage of the bacterial strain through cancer cells in vitro is particularly useful when solid tumor cancer specimens are not available. This makes the invention useful where the cancer cells are harvested from sources including but not limited to patient blood (circulating tumor cells), sputum (lung cancer), vaginal or endocervical swabs, malignant ascites, and malignant pleural effusions.

It is understood that it is feasible to select individualized bacteria for each person's cancer, the only requirement being the availability of cancer cells. Individual cells may be harvested according to the above and other embodiments. If sufficient tumor material is available, such as from a resection, in vivo growth of the tumor tissue is usually feasible with modern techniques in immunodeficient mice or other experimental animals wherein the "designer" bacteria can be selected. With lesser amounts of material, down to individual cells, the "designer" bacteria can be selected in vitro.

The invention provides for an individually-specific strain of further modified attenuated cancer-specific cytotoxic bacteria; derived from *S. typhimuruim* A1 in this particular embodiment. It is appreciated that other species and strains may also be used. It is further understood that throughout this application, where the singular "strain" is written, other embodiments may be practiced with any one of multiple strains of modified bacteria; similarly, where the plural "strains" is used, an embodiment may use a single strain of bacteria The invention utilizes methods 10 and 20 to select the modified strain by passage through experimental animal tumor xenografts until the most tumor-specific tumoricidal variant strain for that individual patient's cancer is created.

According to methods 10 and 20, a fresh portion of tumor harvested by surgical resection or biopsy is transplanted subcutaneously into a quantity of nude mice. Mice of the NOOD.CB17-Prkd$^{cscid}$/NcrCrl ("NOD/SCID") type may be used; other experimental animals may otherwise be available. This cohort of engrafted animals serves to preserve and propagate the human cancer tissue for the single or multiple sequential passaging of the sequential *S. typhimuruim* A strains. These "reselected" strains are denoted A1-R, A1-R$_1$, A1-R$_2$, A1-R$_3$, A1-R$_n$, A1-R$_{n+1}$, etc. "A1" denotes the *S. typhimurium* dual auxotroph strain for Leu-Arg. The invention anticipates other auxotrophs and non-auxotrophic genetic mutations may also be used. The xenografts are allowed to become established, which may occur after any number of days depending on the cell type of the tumor and its individual phenotype. Not all transplanted tumors will "take" in the experimental animal, although the prior art describes in detail methods creating optimal conditions for successful orthotopic grafting.

For embodiments of the method 10 utilizing one or more than one selection cycles in vitro, a portion of xenograft is resected, homogenized in phosphate buffered saline solution ("PBS"), and a suspension of individual cancer cells is prepared using standard techniques known to persons of skill in the art. Certain embodiments may use cancer cells from a non-solid tumor source including but not limited to patient blood (circulating tumor cells), sputum (lung cancer), vaginal or endocervical swabs, malignant ascites, and malignant pleural effusions. In one embodiment, the tumor tissue is homogenized and diluted with PBS. Aliquots containing a quantity of cancer cells are placed in wells containing buffered tissue culture media and grown using standard tissue culture techniques to an approximate density of $10^4$ per well. In other embodiments, any range of cancer cell densities from a single cell may be used, although a preferred range is $10^1$ to $10^6$ cells per well. The wells are then inoculated with a quantity of parent strain *S. typhimurium* A1 or A1-R$_n$, depending on whether the selection cycle is the initial selection using the A1 strain, or an A1-R$_n$ strain from a subsequent passage cycle.

In embodiments of methods 10 and 20 utilizing bacteria labeled with GFP, the parent strain is labeled using established techniques within the body of prior art. In one example from the prior art, the parent strain is grown at 37° C. to mid logarithmic phase in Luria-Bertani ("LB") medium and harvested at 4° C. A quantity of cells ($2.0 \times 10^8$) in 40 μL glycerol (10%) are mixed with 2 μL of the pGFP vector and placed on ice for 5 minutes before electroporation with a Gene Pulser apparatus according to the manufacturer's instructions.

After a period of incubation, cancer cells containing intracellular bacteria and exhibiting signs of apoptosis are selected from the original inoculated aliquots. The selected strain is denoted as A1-R$_{n+1}$. Embodiments of the invention may use A1 or A1-R$_n$ transfected to express GFP to infect tumor xenografts expressing RFP in the cytoplasm and GFP in the nucleus through retroviral transfection, also using standard techniques previously disclosed and known to those with skill in the art. In this manner, only bacteria that are phenotypically 1) able to successfully infect individual cancer cells; and 2) kill those infected cells are selected from the larger population of A1 mutated bacteria. Alternatively, one may choose to use other mutated strains in other embodiments of the invention.

In still another embodiment of methods 10 and 20, tumor-infecting bacteria present following any xenograft passage cycle are selected using an adherence and invasion assay. In these embodiments, the adherence and invasion assay is performed to select the initial strain based upon enhanced tumor targeting. In an example adherence and invasion assay from the prior art, A1 or A1-R$_n$ bacteria are grown to late-log phase in LB broth. The bacteria are diluted in cell culture medium to a concentration of $1 \times 10^6$, added to the cancer cells in tissue culture wells and placed in an incubator at 37° C. After 60 minutes, the cells are rinsed five times with 1 to 2 mL PBS. Adherent bacteria are released by incubation with 0.2 mL 0.1% Triton X-100 for 10 minutes. LB broth (0.8 mL) is then added, and each sample is vigorously mixed. Adherent bacteria are quantified by plating in order to count CFUs on LB agar medium. To select based on invasion, the bacterially-infected cancer cells are rinsed five times with 1 to 2 mL PBS and cultured in a medium containing gentamicin sulfate (20 μg/mL) to kill external but not internal bacteria. After incubation with gentamicin for 12 hours, the cells are washed again with PBS.

The cancer cells containing the A1-R$_n$ bacteria are homogenized and the supernatant plated onto LB or other nutrient-enriched media to accommodate the requirements of the auxotroph, and incubated at 37° C. until growth is observed. This is usually apparent after overnight incubation. Embodiments of the invention utilizing a GFP-expressing bacterial strain allow for more reliable selection of the desired bacteria whereby the plates are examined under an excitatory light source, such as a blue LED. The colonies originating from the selected-tagged bacteria will fluoresce brightly. Regardless of whether this technique is used, the one colony appearing to be pure and growing the most vigorously (or the GFP-expressing colony that fluoresces most brightly) is further selected for propagation in appropriate media using standard techniques. This strain, selected from the parent strain of *S. typhimurium* for its ability to infect and kill cells from the specific individual malignancy of interest, is denoted A1-R$_n$.

For each successive xenograft passage cycle, a quantity of the strain A1-R$_n$ is then inoculated into an experimental animal(s) containing an established cancer tissue graft (xenograft). By way of example, $5 \times 10^7$ CFU is used, but this concentration may be varied in other embodiments of the invention. In alternative embodiments of the invention, the bacterial inoculation is intravenous (tail vein injection), or directly intra-tumoral. Following a period of incubation, generally one to five days, the xenograft or a portion thereof is excised and the tissue is homogenized and diluted in PBS using established techniques. The suspension of cellular debris is allowed to settle and the supernatant is then plated onto LB agar or other media to accommodate the nutrient requirements of the auxotroph. Following an adequate period of incubation (overnight is typical), colonies are again selected for apparent purity and vigor. Again, colony fluorescence is a useful adjunct to selection if GFP or other labeled bacteria are used. The single most vigorous, or most brightly fluorescing where GFP is used, colony is selected. The selected colony is then propagated in LB or other appropriate media using standard techniques. This strain, further selected from the *S. typhimurium* A1-R$_n$ for its ability to target and infect the tumor of interest, is denoted A1-R$_{n+1}$.

The modified strain of *S. typhimurium* A1-R$_n$ (*S. typhimuruim* A1-R$_{n+1}$) that results is more tumor-specific for that individual from whom the original cancer was harvested than the preceding strain A1-R$_n$. The foregoing discussion also discloses the method for creating the strain of enhanced cancer cell-targeting bacteria for individualized cancer therapy. In this invention, the enabling disclosure of the modified strain is by disclosure of the method for its creation.

In still other embodiments of the invention according to methods 10 and 20, the individual tumor-targeting capacity of strain A1-$R_1$ is enhanced by additional passage of sequential strains (i.e. $R_2$, $R_3$, etc.) through tumor xenografts in the established cohort of nude mice (or other experimental animals). This is accomplished by serial repetition of the final four steps: inoculation of a quantity of said bacteria$_{R1}$ into a said experimental animal containing established said cancer tissue graft; removing said cancer tissue graft form the third said experimental animal following a period of in-vivo incubation; extracting bacteria$_{R2}$ from said cancer tissue graft removed from the experimental animal; and incubating said bacteria$_{R2}$ under conditions suitable for bacterial multiplication.

In this way, the invention overcomes a lack of specificity of attenuated strains of facultative anaerobic bacteria, such as *S. typhimuruim* A1, for infecting a specific tumor arising in a unique individual. The invention exploits the retention of individual diversity and genetic heterogeneity demonstrated by orthotopic tumorgrafts (xenografts) in nude mice (or other suitable experimental animal) by selecting for those bacteria with the highest infectivity for that tumor's genetically unique population of malignant cells. The selection process may be facilitated by multiple sequential passage of the chosen bacterial strain through tumor xenografts until selection of the most tumoricidal variant results.

It is understood that although the modified strain of bacteria selected by passage through tumor grafts in experimental animals and/or cancer cells in vitro exhibits enhanced cancer cell targeting of a specific malignancy arising in a unique individual compared to a corresponding unmodified strain of bacteria, this enhanced cancer cell targeting is not necessarily limited to that individual malignancy.

With regard to labeling of the bacteria, methods 10 and 20 may each include various types of labeling. For example, and without limitation, the bacteria may be labeled with a fluorescent label; the bacteria may be labeled with a fluorophore; the bacteria is labeled with a fluorescent protein; and the bacteria is labeled with a fluorescent antibody.

With regard to labeling the harvested cancer cells, methods 10 and 20 may each include labeling the nuclei of the harvested cancer cells with a fluorescent label; labeling the nuclei of the harvested cancer cells with a fluorophore; labeling the nuclei of the harvested cancer cells with a fluorescent protein; and labeling the nuclei of the harvested cancer cells with a fluorescent antibody. Further, methods 10 and 20 may comprise labeling the cytoplasm of the harvested cancer cells with a fluorescent label; labeling the cytoplasm of the harvested cancer cells with a fluorophore; labeling the cytoplasm of the harvested cancer cells with a fluorescent protein; and labeling the cytoplasm of the harvested cancer cells with a fluorescent antibody. Finally, according to methods 10 and 20, labeling nucleus and the cytoplasm of the harvested cancer cells with fluorescent labels.

While the present invention has been shown for the treatment of cancer generally, particular embodiments are useful in the treatment of specific malignancy, such as, a pancreatic cancer, a sarcoma, a lung cancer, a breast cancer, a colon cancer or a prostate cancer.

The embodiments and examples set forth herein were presented in order to best explain the present invention and its practical application, and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above, and are intended to fall within the scope of the appended claims.

What is claimed is:

1. A method for creating a strain of enhanced cancer cell-targeting bacteria for individualized cancer therapy, said method comprising:
    (a) harvesting cancer cells from an individual;
    (b) transplanting a quantity of said cancer cells into a quantity of experimental animals;
    (c) incubating the experimental animals to establish a cancer tissue graft within the experimental animals;
    (d) inoculating a *Salmonella typhimurium*$_{A1}$ into a said experimental animal containing established said cancer tissue graft;
    (e) removing said cancer tissue graft from said experimental animal inoculated with said *Salmonella typhimurium*$_{A1}$ following a period of incubation of the inoculated said experimental animal;
    (f) extracting a *Salmonella typhimurium*$_{A1-R}$ from said cancer tissue graft removed from the experimental animal inoculated with said *Salmonella typhimurium*$_{A1-R}$;
    (g) incubating said *Salmonella typhimurium*$_{A1-R}$ under conditions suitable for bacterial multiplication;
    (h) selecting a said *Salmonella typhimurium*$_{A1-R}$;
    (i) incubating the selected said *Salmonella typhimurium*$_{A1-R}$ under conditions suitable for bacterial multiplication;
    (j) inoculating a quantity of selected said *Salmonella typhimurium*$_{A1-R}$ into a second said experimental animal containing established said cancer tissue graft;
    (k) removing said cancer tissue graft from the said experimental animal inoculated with a quantity *Salmonella typhimurium*$_{A1-R}$ following a period of incubation;
    (l) extracting *Salmonella typhimurium*$_{A1-R}$ from said cancer tissue graft removed from the experimental animal;
    (m) incubating said bacteria$_{R1}$ under conditions suitable for bacterial multiplication; and
    (n) selecting a *Salmonella typhimurium*$_{R1}$.

2. The method of claim 1 wherein said enhanced cancer cell-targeting bacteria is created by at least one passage through cancer cells in vitro.

3. The method of claim 1 wherein the *Salmonella typhimurium*$_{A1}$ is auxotrophic for one or more essential nutrients.

4. The method of claim 1 wherein the *Salmonella typhimurium*$_{A1}$ is auxotrophic for arginine and leucine.

5. The method of claim 1 further comprising creating additional strains of enhanced cancer cell-targeting *Salmonella typhimurium*$_{A1}$ in response to repeating a portion of the method n additional times sequentially with strains of said *Salmonella typhimurium*$_{A-Rn}$.

6. The method of claim 1 further comprising labeling the *Salmonella typhimurium*$_{A1}$ with a fluorescent label.

7. The method of claim 1 further comprising labeling the *Salmonella typhimurium*$_{A1}$ with a fluorophore.

8. The method of claim 1 further comprising labeling the *Salmonella typhimurium*$_{A1}$ with a fluorescent protein.

9. The method of claim 1 further comprising labeling the *Salmonella typhimurium*$_{A1}$ with a fluorescent antibody.

10. The method of claim 1 further comprising labeling the nuclei of the harvested cancer cells with a fluorescent label.

11. The method of claim 1 further comprising labeling the nuclei of the harvested cancer cells with a fluorescent protein; and a fluorescent antibody.

12. The method of claim 1 further comprising labeling cytoplasm of the harvested cancer cells with a fluorescent label.

13. The method of claim 1 further comprising labeling cytoplasm of the harvested cancer cells with a fluorophore.

14. The method of claim 1 further comprising labeling cytoplasm of the harvested cancer cells with a fluorescent protein.

15. The method of claim 1 further comprising labeling cytoplasm of the harvested cancer cells with a fluorescent antibody.

16. The method of claim 1 further comprising labeling the nucleus and the cytoplasm of the harvested cancer cells with fluorescent labels.

17. The method of claim 1, wherein said cancer cells are a pancreatic cancer.

18. The method of claim 1, wherein said cancer cells are a sarcoma.

19. The method of claim 1, wherein said cancer cells are a lung cancer.

20. The method of claim 1, wherein said cancer cells are a breast cancer.

21. The method of claim 1, wherein said cancer cells are a colon cancer.

* * * * *